(12) United States Patent
Worsoee

(10) Patent No.: US 8,007,482 B2
(45) Date of Patent: *Aug. 30, 2011

(54) PRE-FILTER FOR AN OSTOMY BAG

(75) Inventor: Bjarne Worsoee, Tikoeb (DK)

(73) Assignee: Coloplast A/S, Humlebaek (DK)

( * ) Notice: Subject to any disclaimer, the term of this patent is extended or adjusted under 35 U.S.C. 154(b) by 773 days.

This patent is subject to a terminal disclaimer.

(21) Appl. No.: 11/922,754

(22) PCT Filed: Jun. 28, 2006

(86) PCT No.: PCT/DK2006/000382
§ 371 (c)(1),
(2), (4) Date: Dec. 21, 2007

(87) PCT Pub. No.: WO2007/000167
PCT Pub. Date: Jan. 4, 2007

(65) Prior Publication Data
US 2009/0171306 A1  Jul. 2, 2009

(30) Foreign Application Priority Data
Jun. 28, 2005  (DK) ................... 2005 00963

(51) Int. Cl.
*A61F 5/44* (2006.01)
(52) U.S. Cl. ........ 604/333; 604/331; 604/332; 604/334; 604/335; 604/336; 604/337; 604/338; 604/339; 604/341; 604/359; 604/360
(58) Field of Classification Search ................ 604/333, 604/331, 332, 334–339, 341, 359, 360
See application file for complete search history.

(56) References Cited

U.S. PATENT DOCUMENTS

| 4,387,712 A | 6/1983 | Briggs et al. | |
|---|---|---|---|
| 4,411,659 A | 10/1983 | Jensen et al. | |
| 4,479,818 A | 10/1984 | Briggs et al. | |
| 5,306,264 A * | 4/1994 | Ferguson et al. | 604/333 |
| 5,643,234 A * | 7/1997 | Lesko | 604/333 |
| 5,672,163 A | 9/1997 | Ferreira et al. | |
| 5,690,622 A * | 11/1997 | Smith et al. | 604/333 |
| 5,733,271 A * | 3/1998 | Bjørn | 604/333 |
| 6,129,716 A * | 10/2000 | Steer | 604/333 |
| 6,135,986 A * | 10/2000 | Leisner et al. | 604/322 |
| 7,435,380 B2 * | 10/2008 | Winston | 422/27 |

(Continued)

FOREIGN PATENT DOCUMENTS

DE  36 08 933  10/1987
(Continued)

*Primary Examiner* — Melanie J Hand
*Assistant Examiner* — Ginger T Chapman
(74) *Attorney, Agent, or Firm* — Coloplast Corp., Coloplast A/S; Daniel G. Chapik; Nicholas R. Baumann

(57) ABSTRACT

An ostomy bag with a filter assembly having a gas filter and a pre-filter for preventing or delaying solid/semisolid matter and liquid from reaching the gas filter. The pre-filter is at least substantially flat and comprises a number of constrictions, such as ribs extending along and between two inner surface parts of the channel. These constrictions/ribs form narrower and wider passages where the gas may more quickly pass a narrow passage and where the wider passages tend to receive and hold the liquid, solid matter and semisolid matter. At least a part of the constrictions may be provided in a random pattern.

12 Claims, 4 Drawing Sheets

U.S. PATENT DOCUMENTS

Figure 1:
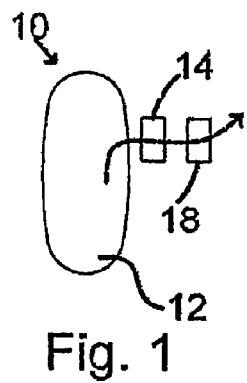

| | | | |
|---|---|---|---|
| 7,789,866 B2 * | 9/2010 | Poulsen et al. | 604/333 |
| 2003/0014023 A1 | 1/2003 | Kanbara | |

FOREIGN PATENT DOCUMENTS

| | | |
|---|---|---|
| EP | A-0 116 363 | 8/1984 |
| EP | 0 475 608 | 3/1992 |
| EP | 0 607 028 | 7/1994 |
| WO | WO 98/44880 | 10/1998 |
| WO | WO 01/34072 | 5/2001 |
| WO | WO 03/020118 | 3/2003 |
| WO | WO 03/020188 A1 * | 3/2003 |
| WO | WO 2005/063146 | 7/2005 |
| WO | WO 2005/063146 A2 * | 7/2005 |

* cited by examiner

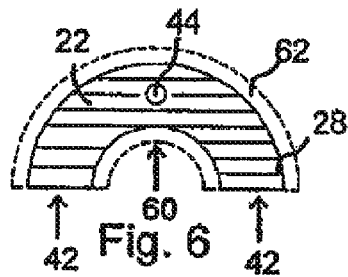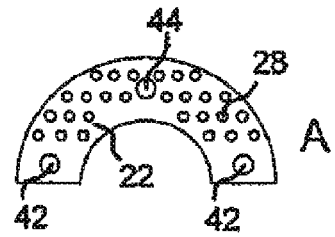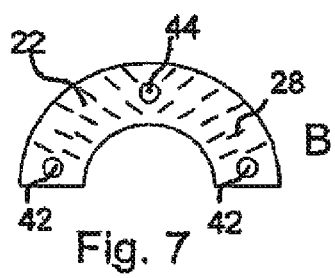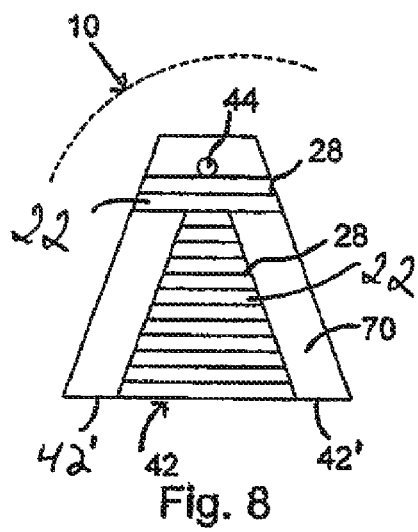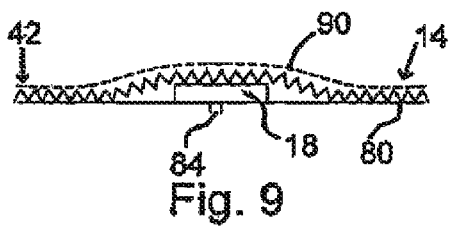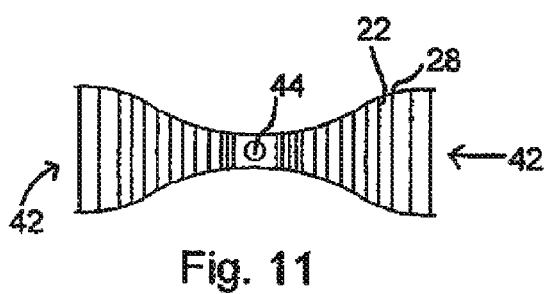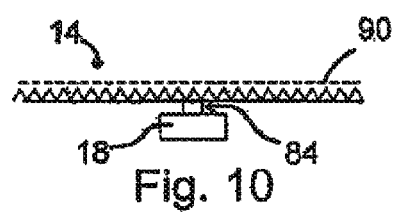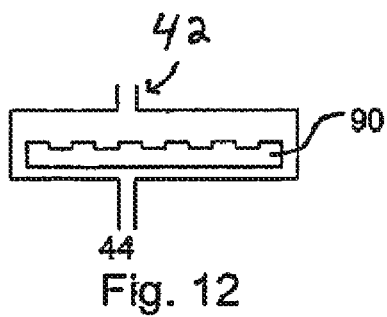

PRE-FILTER FOR AN OSTOMY BAG

This is a national stage of International Application No. PCT/DK2006/000382 filed on Jun. 28, 2006 and published in English.

The present invention relates to an ostomy receiving bag having a gas filtering assembly comprising a gas filter and a pre-filter defining a plurality of restrictions between two opposed substantially liquid impermeable surfaces.

The normally used gas filter is a filter with a surface of activated carbon. This filter is sensitive to liquids and should preferably be kept dry. This can be done by means of a pre-filter which prevents solid/semisolid material and liquid from the ostomy bag from reaching the gas filter.

Pre-filters of open cell foams are known in the art. Such pre-filters define multiple meandering gas paths from the ostomy bag to the gas filter. The foams, however, are not easily standardized, and the individual gas paths will comprise narrow parts which are easily clogged. One example of such a filter is known from EP-A-0 607 028.

Another kind of pre-filter defines a plurality of restrictions between two opposed surfaces are disclosed in the applicants own application PCT/DK2004/000919 which was not published at the time of filing the present application.

Other ostomy appliances may be seen in WO98/044880, WO03/020118, WO 01/34072, US 2003/0014023, U.S. Pat. Nos. 4,387,712, 4,411,659 and EP-A-0 116 363.

Thus, in a FIRST aspect the present invention relates to an ostomy appliance comprising a collecting bag and a gas filtering assembly positioned in a gas path from an interior of the collecting bag to the surroundings,
the gas filtering assembly comprising, in the flow direction of the gas from the interior to the surroundings, a pre-filter and a gas filter,
wherein the pre-filter comprises
  a gas entrance,
  a gas exit, and
  a gas channel defined between the gas entrance and the gas exit, the gas channel having two opposed, at least substantially liquid impermeable surfaces defining there between a number of constrictions each having a predetermined, largest width, wherein the distance between the two opposed surfaces, at the constriction(s), is significantly smaller than the largest width of the constriction,
wherein the at least a part of the constrictions is provided in a random pattern.

The random pattern may be provided in a first direction such as the flow direction of the gas channel or in a direction transverse to the flow direction or a first direction in a plane in which one of the opposed surfaces are provided. Alternatively, at least a part of the constrictions may be provided in a random pattern in both a first and a second direction, the second direction being transverse to the first direction. Accordingly, an area of the pre-filter may define constrictions in a random pattern.

In one embodiment the distance between the constrictions in the first direction, e.g. the flow direction, varies in a random pattern. In this embodiment the distance between the opposed surfaces at each constriction may be identical and, thus, only the distance between the constrictions in the flow direction varies in a random pattern.

In another embodiment the distance between the two opposed surfaces, at the constrictions, varies in a random pattern along the first direction. In this embodiment the distance between the two opposed surfaces varies while the distance between each constriction in the first direction is identical.

In yet another embodiment the distance between the opposed surfaces at each constriction varies in a random pattern while at the same time the distance between the constrictions in the first direction (e.g. coinciding with the flow direction) also varies in a random pattern.

At least a part of one of the opposed surfaces may comprise a closed-cell foam. As an example the entire surface of one of the surfaces may comprise a closed-cell foam. In one embodiment a part of both of the surfaces comprises a closed-cell foam such as the entire surface of both the two opposed surfaces.

In the context of the present invention the term foam is defined as a substance that is formed by trapping gas bubbles in a liquid or solid. The foam is produced by the formation of bubbles in a liquid and causing the liquid to solidify. Foams may be distinctive by the number of air bubbles per distance e.g. bubbles per inch. Foams may be closed-celled and open-celled. An open-cell foam is a foam wherein most of the sidewalls between the bubbles are removed e.g. by exploding the gas-bubbles. The exploded gas-bubbles are typically referred to as pores and when referring to open-cell foams it is often with reference to the number of pores per inch (PPI). Closed-cell foams are however typically referred to by its weight in grams per cubic centimeter ($g/cm^3$). Although these references are not standards, they are widely used.

In the present invention the number of bubbles per inch may be between 5 and 50, such as 10 or 15 or 20 or 25 or 30 or 35 in the closed cell foam. The thickness of walls between two bubbles may be between a $20^{th}$ and a third of the largest dimension of the bubble.

The outer surface of the closed-cell foam may define a plurality of cavities, i.e. bubbles which are not completely enclosed by the material of which the foam is made. The size of the cavities may vary along the surface of the foam.

In a SECOND aspect the present invention relates to a method of making a pre-filter according to the first aspect of the invention, the method comprising the steps of:
  providing an pre-filter element comprising an uneven surface, and
  assembling the pre-filter, such that the uneven surface defines one of the surfaces of the pre-filter.

In one embodiment the step of providing a pre-filter element may comprise the steps of providing a first pre-filter element comprising an uneven surface and providing a second pre-filter element comprising an uneven surface. Furthermore, the step of assembling the pre-filter may comprise the step of assembling the first and second pre-filter element such that there is provided a plurality of constrictions there between.

The pre-filter element may be a closed-cell foam.

Alternatively part of or the entire surface of the closed-cell foam, which is to function as the uneven surface be heat treated. This will burn away some of the walls in the closed-cell foam which will create larger and more distinct cavities in the surface, while still maintaining a random pattern of cavities and thereby also a random pattern of the constrictions.

This treatment can for example be done by gas burning the surface, i.e. using a gas flame that is displaced along the surface of the closed-cell foam. Depending on the temperature of the flame, which can be several hundred degrees Celsius and the distance to the surface, this treatment can be performed very quickly.

Above heat treatment could for example also be performed by laser and many other heat generating sources known in the art.

According to a THIRD aspect, the present invention relates to use of an item having an uneven surface for defining a plurality of constrictions in a random pattern in a pre-filter for an ostomy appliance, the pre-filter being according to the first aspect of the present invention. The item may be a closed-cell foam.

In the following the invention is described in further detail. The description relates to the first, second and third aspect of the present invention.

In the present context, the distance is "significantly smaller" if it is less than 75% of the largest width of the constriction. It should be noted that this distance preferably is determined in a direction perpendicular to a general plane of the opposed surfaces and/or it is determined to be the smallest distance between the surfaces at that point. Naturally, the distance may be less than 50%, such as less than 30%, preferably less than 20%, such as less than 10%, and it may actually be less than that, such as less than 5%, 2%, or even 1% of the width.

This distance, naturally, may vary when the ostomy bag is moved, such as during movement of the user, whereby it may be desired that the distance, in unstressed use or in an unused bag, may be zero. When a gas pressure builds up, this distance may then increase and let the gas through.

It has been found that it is the narrowing provided by the constrictions which actually performs the filtering. The constrictions will provide a channel having narrower and wider portions, where the solid/semisolid material and liquid from the ostomy bag will tend to assemble in the wider portions between the constrictions. This function is opposed to that of U.S. Pat. No. 4,411,659, where the gas travels between the grid of the ribs and the liquid/solid/semisolid matter falls between the ribs due to gravity alone.

Normally, the gas filter is adapted to filter odour from the gas, such as a filter comprising activated carbon.

When the surfaces of the gas channel are at least substantially liquid impermeable, liquid entering the gas channel will tend to remain therein (or at least exit via the gas entrance/exit). If the sides were too liquid permeable, too much liquid could enter the gas channel close to the gas exit and thereby avoid the constrictions and the filtering effect thereof.

However, the surfaces may be gas permeable so that gas may enter close to the gas exit and exit via the gas exit without reducing the efficiency or operation of the pre-filter.

Preferably, the gas channel is oblong, such as oblong in the plane of one of or both of the opposed surfaces. Preferably, the channel is oblong in the direction of the gas flow—from the entrance to the exit. Also, the gas channel may be at least substantially flat. In the present context, "substantially flat" will mean that the channel extends considerably, such as at least a factor of 1.5, such as at least 2, preferably at least a factor of 5, more in the directions of the opposed surfaces than in a direction between these surfaces. Generally, the "direction of gas flow" will be the overall direction of gas flow from entrance to exit not taking notice of the meandering paths gas may take from entrance to exit.

Preferably, a largest distance between the constriction and a neighbouring constriction is at least 1.5 times the distance between the two opposed surfaces at the constriction, such as at least 2 times the distance, preferably at least 4 times the distance between the two opposed surfaces at the constriction.

The constrictions are preferably oblong elements. The constrictions may or may not have the same cross section and size/length. The distances between pairs of the constrictions may be the same (equidistant spacing) or may differ (be periodic or not). Normally, oblong constrictions will extend in at least substantially the same direction (be at least substantially parallel), but also other types of patterns are possible. Non-oblong constrictions may e.g. be positioned in a predetermined pattern in the gas channel. It is preferred that the constrictions do not overlap in that this may provide openings through which the liquid/solid/semisolid matter may more easily flow toward the gas filter.

In one embodiment, at least one of the constrictions comprises a rib extending along one of the opposed surfaces. In this connection, a "rib" will be an oblong constriction having at least substantially the same cross-section along its length.

In one situation, the ribs extend along the direction of flow in the gas channel. In this manner, the ribs will, there between, form a plurality of gas paths along the gas channel. If one path is blocked, the gas may travel under or around one of the ribs of that path and into another path and continue toward the gas filter.

In another embodiment, the ribs extend across the direction of flow in the gas channel. In this situation, the ribs form intermittent narrower and wider passages which the gas must pass order to reach the gas filter. The wider passages will act to retain matter/liquid due to the gas more easily passing the narrower paths generated by the ribs.

An interesting aspect is one where at least one of the constrictions has a cross section having, at one side thereof, a concave part adapted to receive solid or liquid material. Preferably, this concave part is provided on a side of the constriction facing in the direction of the gas flow. In that situation, the concave part may then actually take up and/or hold the liquid/solid/semisolid matter.

In general, both the gas filter and the pre-filter may be present in the ostomy bag, they may both be positioned outside the ostomy bag, or the pre-filter may be positioned inside the ostomy bag and the gas filter may be positioned outside the ostomy bag.

In one embodiment, where both filters are present in the ostomy bag, the pre-filter may fully overlap the gas filter so that no part of the gas filter is directly exposed to the interior of the ostomy bag.

In addition, the two filters may be covered by an impermeable film being attached to the bag wall and defining entrances for the gas/liquid/solid/semisolid matter to the pre-filter. Another manner is one where the filters are covered by a non-woven material, a net, a perforated material or a micro porous membrane which allows gas to pass and which is blocked when faeces tries to enter. Thereafter, further liquid/faeces entry is possible only at the gas entrance. This again gives the desired filtering function.

Naturally, the gas channel may have any desired shape. Presently, it is preferred that the gas channel has a bent shape. This is considered the most suitable shape for use in ostomy bags. However, other shapes, such as round, oval, oblong, and an S-shape may be used. Normally, this shape is determined in the general plane of the opposed surfaces.

The constrictions may be provided only at a predetermined area of the opposed surfaces of the gas channel. In that situation, another area of the surfaces may be free from constrictions and thereby form a wide gas channel. This constriction-free part may be provided close to the gas outlet of the pre-filter and is preferably positioned at a higher position, in relation to the majority of the pre-filter constrictions in order to have liquid/solid/semisolid matter, due to gravity, tend to stay away from the gas exit and the gas filter.

Naturally, the constrictions in the gas channel may have different lengths. In one embodiment, the longer constrictions are positioned closer to the entrance than the constrictions of shorter length. In this manner, the longer constrictions forming longer channels for receiving and holding liquid/solid/semisolid matter are positioned closer to the entrance through which the liquid/solid/semisolid matter enters.

Also, the distance between constrictions may vary over the area of the opposed surfaces. In a preferred manner, the distance is larger closer to the gas entrance in order to form larger reservoirs for holding liquid/solid/semisolid matter close to the entrance where it enters the pre-filter.

The constrictions may be provided in a wide variety of manners. One manner is the providing of the constrictions by forming these in e.g. a foil forming one of the two opposed surfaces of the gas channel. This forming may be a deformation, such as one based on heating and stretching of the foil. In that manner, a very simple manufacture of the present pre-filter is obtained (such as by simply combining this deformed foil and a straight foil).

Another manner is to provide the constrictions between two foils, where the gas channel is then formed between the constrictions and one of the foils. If the constrictions are provided as individual constrictions, the gas channel will be formed by one of the opposed surfaces being one foil and the other opposed surface being formed by the constrictions and the other foil.

In another embodiment, however, the constrictions are provided as a monolithic element. Then, the gas channel is formed by, on the one side, the monolithic element, and, on the other side, a part of the appliance, such as a foil thereof. This eases the manufacture and assembly of the filter assembly and ostomy bag. The monolithic element may be prepared in any suitable manner, such as by extrusion, moulding or the like.

In one embodiment, the monolithic element further comprises means for engaging or attachment to a part of the bag so as to define the gas channel between the monolithic element and the part of the bag. In that manner, the gas channel is defined by the wall and the monolithic element of the pre-filter, which makes the manufacture and assembly quite fast. This corresponds to replacing the above deformed foil by the monolithic element. The engaging means may be parts without constrictions and which are attachable directly to the bag wall using heat welding, laser welding, HF welding, adhesives or the like.

Also, it may be desired that the monolithic element is at least substantially flat having two main sides, and has one or more constrictions on each of the two main sides. In that manner, two parallel gas channels may be formed, whereby the filtering may be performed on both sides of the element.

Figure 2:
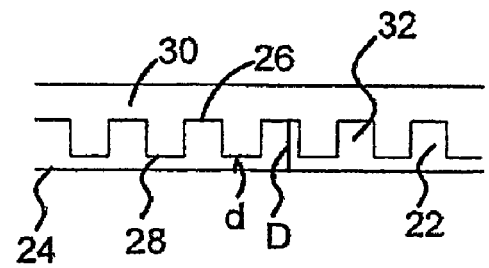
Figure 3:
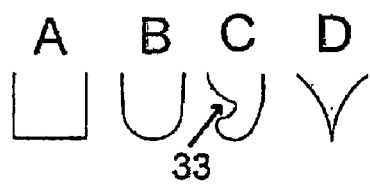
Figure 4:
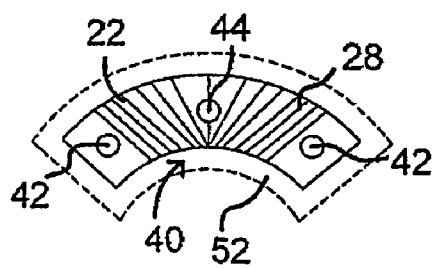
Figure 5:
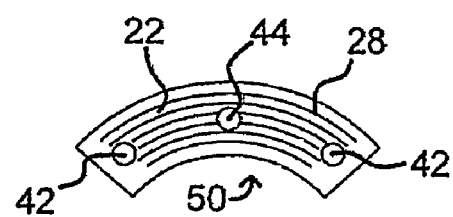
Figure 13A:
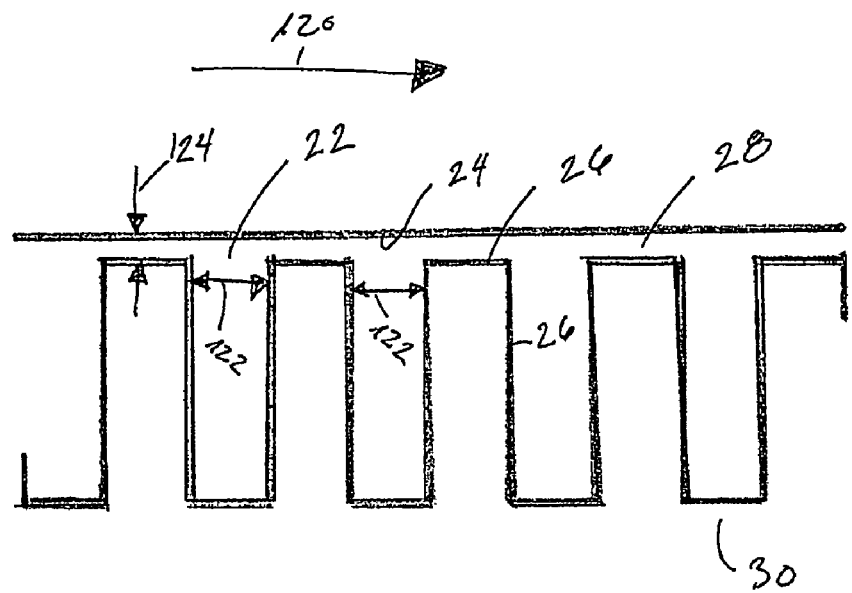
Figure 13B:
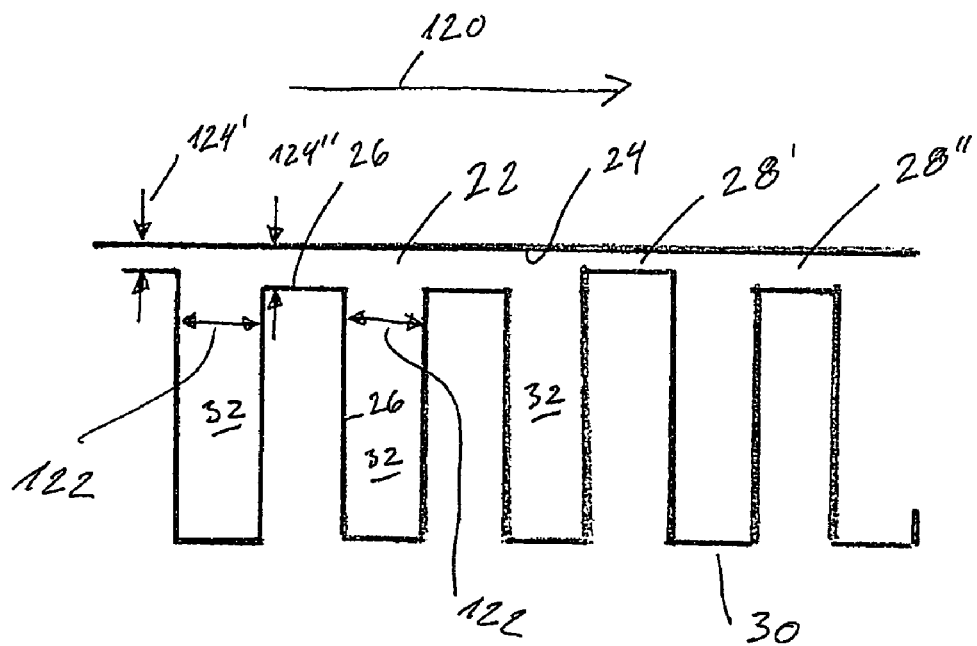
Figure 13C:
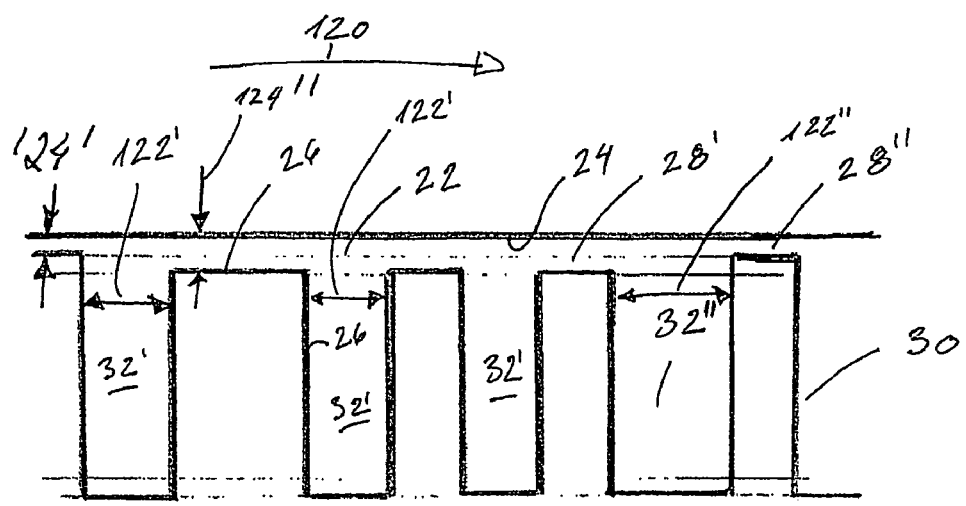
Figure 14:
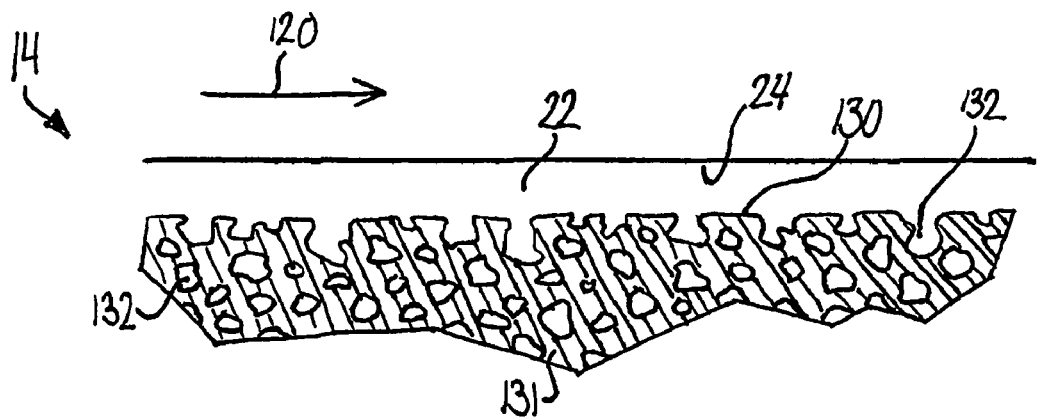

In the following, exemplary embodiments of the invention will be described with reference to the drawing, wherein:

FIG. 1 illustrates a cross section of an ostomy bag with a gas filter and a pre-filter, FIG. 2 illustrates a first embodiment of the pre-filter, FIG. 3 illustrates different cross sections of constrictions, FIG. 4 illustrates, seen from above, a second preferred embodiment of a pre-filter, FIG. 5 illustrates, seen from above, a third preferred embodiment of a pre-filter, FIG. 6 illustrates, seen from above, a fourth preferred embodiment of a pre-filter, FIG. 7 illustrates, seen from above, a fifth preferred embodiment of a pre-filter, FIG. 8 illustrates an embodiment of the pre-filter wherein a constriction-free areas are used, FIG. 9 illustrates a first embodiment with a first position of the gas filter and the pre-filter, FIG. 10 illustrates a second embodiment with another position of the gas filter and the pre-filter, FIG. 11 illustrates yet another embodiment of a pre-filter, FIG. 12 illustrates another embodiment of a pre-filter, FIG. 13*a* illustrates a pattern, FIGS. 13*b*-13*c* illustrate different random patterns, and FIG. 14 illustrates random patterns provided by a closed-cell foam.

In FIG. 1, the overall structure of an ostomy bag of the present type is illustrated in a cross section. It is seen that the bag 10 has a container 12, and, in the direction of flow of the gas from the container 12 to the surroundings as illustrated by the arrow, a pre-filter 14 and a gas filter 18.

The function of the gas filter 18 is to deodorize the gas received from the stoma (not illustrated). Normally, this gas filter 18 is an open cell foam comprising activated carbon for performing the actual deodorization. The gas filter may also comprise a membrane. Gas filters and membranes of this type may be seen in WO98/44880 and WO03/020188.

The function of the pre-filter 14 is to prevent or delay the liquids and solid/semisolid matter in the container 12 from reaching the filter 18.

FIG. 2 illustrates a first embodiment of the pre-filter 14 according to the invention. This pre-filter 14 comprises a gas channel 22 defined by a first surface 24 and a second surface 26 forming a number of constrictions 28. In fact, the constrictions 28 and surface 26 are preferably parts of the same ribbed, monolithic element 30. In the present embodiment, the gas channel 22 is flat and extends in the left/right direction (direction of flow of the gas as illustrated by the arrow) and the direction out of the plane of the figure.

The function of the constrictions 28 is that when gas travels in the direction of the arrow together with liquid and solid/semisolid matter, the gas will tend to force the liquid/solid/semisolid matter under the constrictions 28 toward the gas filter 18. However, due to the constrictions 28, the gas will travel more easily than the liquid/solid/semisolid matter, whereby the liquid etc. will, tend to accumulate in the spaces 32 between the constrictions 28 and be stored instead of immediately being forced under the next constriction 28.

The amount of liquid/solid/semisolid matter which may be stored in a space 32 depends, naturally, on the height, D, of the space and the distance between the two constrictions 28.

It is clear that the filter 14 may be widened in the direction out of the plane of the figure in order to increase the amount of gas filterable.

Also, it is clear that the filtering characteristics of the filter 14 may be controlled by e.g. the distance, d, between the constrictions 28 and the surface 24. When gas has to pass the pre-filter, a pressure is built up. Thus, the distance, d, between the constrictions 28 and the surface 24 may be zero (in an unused or unbiased state), so that the pressure itself forces the gas under the constrictions 28.

Also, as is clear from FIG. 3, an infinite number of different cross sections of the constrictions 28 may be used. Naturally, the shape of the constriction 28 will determine the gas filtering characteristics both when the person carrying the bag 10 is resting as well as when he/she is moving, whereby the distance, d, between (or the force exerted between) the constrictions 28 and the surface 24 changes.

An interesting cross section is illustrated in FIG. 3C, where a concave part 33 is provided. This concave part will act to collect and hold liquid/solid/semisolid matter and is preferably positioned on a side facing the gas flow direction (facing toward the gas exit).

FIG. 4 illustrates, seen from above, the overall structure of a preferred embodiment of the pre-filter and the gas flow therein.

The pre-filter 40 is bent and has a gas entrance 42 at each end and a gas exit 44 toward the entrance of the gas filter at the middle. The pre-filter 40 has a plurality of rib-shaped constrictions 28 extending across the gas flow direction between the entrances 42 and the exit 44.

In this embodiment, the gas and liquid/solid/semisolid matter must pass the ribs 28, and the liquid/solid/semisolid matter will, firstly, not be able to travel as swiftly under the ribs 28 as the gas, whereby the desired delay is desired. Secondly, the channels 22 between the ribs 28 will tend to receive and hold the liquid/solid/semisolid matter, whereby an additional delay is obtained.

In FIG. 4, a cover sheet 52 is illustrated for overlapping the pre-filter 40 and for actually defining the entrances 42. This sheet 52 prevents gas/liquid/solid/semisolid matter from shortcutting through the pre-filter 40.

Even though the sheet 52 overlays the pre-filter 40, it is preferred that the part of the pre-filter 40 with the ribs 28 is a single monolithic element. This eases the manufacture and assembly thereof.

The pre-filter 40 is preferably moulded due to it not being a standard product with this shape of the ribs 28.

FIG. 5 illustrates another preferred embodiment, where the pre-filter 50 has a number of rib-shaped constrictions 28 which are now oriented along the gas flow direction from the entrances 42 to the exit 44.

The ribs 28 form a number of gas channels 22 through which the gas may flow toward the exit 44. When liquid/solid/semisolid matter enters the pre-filter 40, it will tend to block the channels 22. Then, the gas flowing in a blocked channel 22 may travel under a rib 28 into another, possibly open, channel 22 and maintain its flow toward the exit 44.

FIG. 6 illustrates another preferred embodiment, where the rib-shaped constrictions 28 are again positioned across the gas flow direction in the beginning of the gas flow path in the pre-filter 60 but are at the final path more parallel to the gas flow.

In this embodiment, no sheet 52 is needed in that the pre-filter 60 comprises outer parts 62 where the ribs 28 are not present. These parts 62 are welded to the side of the ostomy bag in order to then define the gas channel. The entrances 42 may be provided by not welding the parts 62 all around the pre-filter 60 or by cutting part of previously provided parts 62 away at those positions prior to welding the remaining parts 62.

When the ribs 28 are parallel, this may be a standard product made as an endless, extruded ribbed band. The pre-filter 60 may be provided by simply cutting the desired shape from the band.

FIG. 7 illustrates two other manners of providing the constrictions. In FIG. 7a, the constrictions 28 are not oblong but more limited in extent. These constrictions preferably have a cross section as that of FIG. 3a in order to obtain an oblong filtering slot between the constriction 28 and the opposed surface 24. These constrictions may be randomly positioned or may be positioned (as illustrated) in a predefined pattern. FIG. 7b illustrates an embodiment using rib-shaped constrictions 28, but where the ribs 28 do not extend from one side to the other of the filter but rather extend only a part of that width. Nevertheless, a good filtering is expected from this filter.

FIG. 8 illustrates an interesting embodiment, where the rib-shaped constrictions 28 and channels 22 do not cover the full area of the gas channel. In this embodiment, two areas 70 are present in which no ribs 28 are present.

In this embodiment, the entrance 42 opens only to the part where the ribs 28 are present and is simply an open end of the pre-filter with direct access to the interior of the ostomy bag.

The areas 70 act to assemble liquid/solid/semisolid matter from the channels 22 and to, if the exit 44 is positioned higher than the entrance 42, either store this therein or to re-emit it to the bag 10 via valves 42', such as lip valves formed by two parts of foil and which act to expel liquid/solid/semisolid matter from the areas 70 and counteract entrance of liquid/solid/semisolid matter from the bag to the areas 70.

Close to the exit 44, the ribs 28 extend across the full width of the gas channel in order to prevent accidental contact between liquid/solid/semisolid matter in the areas 70 and the exit 44 due to e.g. compressing or other movement of the bag 10.

This embodiment also illustrates that it is quite possible to provide different lengths of the ribs 28 and a varying width of the gas channel. It is preferred to have longer ribs 28 at the entrance 42 in order to have longer/larger channels 22 for holding as much liquid/solid/semisolid matter as possible instead of risking early clogging or requiring transport of a large amount of liquid/solid/semisolid matter to other parts of the pre-filter. See also FIG. 11.

FIGS. 9 and 10 illustrate that the filter assembly of the pre-filter 14 and the gas filter 18 may be positioned in a number of places in relation to the ostomy bag wall 80. The choices made in this respect relate mainly to choices of manufacture and not of functionality.

In the embodiment illustrated in FIG. 9, the full assembly is positioned inside the ostomy bag 10. In this embodiment, the gas enters the entrance 42, flows in the pre-filter 14 toward the gas exit of the pre-filter 14. The gas then flows through the gas filter 18 and exits the bag through an exit hole 84 provided in the bag wall 80. The pre-filter 14 covers the gas filter 18 and is welded to the bag wall 80 with weldings as described in relation to FIG. 6.

The pre-filter 14 may be covered by a plastic foil (illustrated by numeral 90) in order to define the gas entrance 42 in order to prevent liquid/solid/semisolid matter from shortcutting the filter 14 and reaching the gas filter 18.

In the embodiment illustrated in FIG. 10, the pre-filter 14 is positioned inside the bag 10, and the gas flow exiting the pre-filter 14 exits the bag wall through a gas exit 84, enters the gas filter 18 positioned outside the bag 10.

In general, just as the length and direction of the ribs/constrictions 28 (and channels 22) are variable, so is the distance between the ribs/constrictions 28 and the wall 24 and between neighbouring ribs/constrictions. Thus, a larger distance between the constrictions and the opposing surface may be desired at least at the entrance 42 in order to, in fact, facilitate transport of liquid/solid/semisolid matter to other parts of the pre-filter (instead of simply clogging the pre-filter), and a smaller distance may be desired closer to the exit 44 or the gas filter 18 in order to prevent liquid/solid/semisolid matter from reaching the exit.

In FIG. 11, again two entrances 42 are present together with the exit 44. The rib-shaped constrictions 28 extend the full width of the gas channel, but now the ribs 28 are longer (wider channel) close to the entrances 42. In addition, the distance between the ribs 28 is larger close to the entrances 42 in order to provide larger channels 22 for assembling and holding liquid/solid/semisolid matter instead of desiring that this liquid/solid/semisolid matter travels into the pre-filter 14 in order to provide space for additional liquid/solid/semisolid matter.

In FIG. 12, another manner of using a pre-filter element 90 is illustrated wherein the gas flow is around the element from a first major side thereof to the other major side thereof. The filtering process is the same, but the overall positions of the entrance 42 and exit 44 differs from the other embodiments.

It is clear from the following, that the features of the individual embodiments (d, D, length of ribs/constrictions, cross section, positioning thereof, the shape of the gas channel, the use of an impermeable sheet/non-woven or the like, welding the pre-filter to the bag, gas filter and/or pre-filter inside or outside the bag, a membrane or not etc.) may be interchanged and used in a large number of ways without deferring from the invention.

FIGS. 13*a*-13*c* illustrate a sectional view of the pre-filter 14 according an aspect of the invention. This pre-filter 14 comprises a gas channel 22 defined by a first surface 24 and a second surface 26 forming a number of constrictions 28,28', 28". In fact, the constrictions 28,28',28" and surface 26 are preferably parts of the same ribbed, monolithic element 30. In the present embodiment, the gas channel 22 is flat and extends in the left/right direction (direction of flow of the gas as illustrated by the arrow) and the direction out of the plane of the figure. Furthermore, in the present embodiment the first direction is indicated by arrow 120 and the second direction is extending in and out of the figure, perpendicular to the first direction.

The function of the constrictions 28, 28', 28" are that when gas travels in the direction of the arrow together with liquid and solid/semisolid matter, the gas will tend to force the liquid/solid/semisolid matter under the constrictions 28, 28', 28" toward the gas filter 18. However, due to the constrictions 28, 28', 28" the gas will travel more easily than the liquid/solid/semisolid matter, whereby the liquid/solid/semisolid matter will tend to accumulate in the spaces 32 between the constrictions 28, 28', 28" and be stored instead of immediately being forced under the next constriction 28, 28', 28".

In FIG. 13*a* distance 122 between the constrictions in the first direction 120 is constant. At the same time the distance 124 between the two opposed surfaces, at the constrictions, is also constant.

In FIG. 13*b* the distance 122 between the constrictions in the first direction 120 is constant, while at the same time the distance 124',124" between two opposed surfaces, at the constrictions, varies in a random pattern.

In FIG. 13*c* the distance 122',122" between the constrictions in the first direction 120 varies in a random pattern, while at the same time the distance 124',124" between two opposed surfaces, at the constrictions, also varies in a random pattern.

Naturally the distance 122',122" may vary while at the same time the distance 124 is constant (not shown).

In another embodiment of the pre-filter 14 shown in a sectional view in FIG. 14, the gas channel 22 is defined by the first surface 24 and a second surface 130 of a-closed cell foam 131. As can be understood the randomness of the cavities 132 in the closed-cell foam will create a random pattern of constrictions along a surface, such as the second surface 130.

The invention claimed is:

1. A pre-filter for a gas filtering assembly for an ostomy appliance, the pre-filter comprising a gas entrance, a gas exit, and a gas channel defined between the gas entrance and the gas exit, the gas channel having two opposed, at least substantially liquid impermeable surfaces defining there between a number of constrictions each having a predetermined, largest width, wherein the distance between the two opposed surfaces, at the constriction(s), is significantly smaller than the largest width of the constriction, wherein at least a part of the constrictions is provided in a random pattern.

2. A pre-filter according to claim 1, wherein the constrictions are provided in a first direction.

3. A pre-filter according to claim 1, wherein at least a part of the constrictions are provided in a random pattern in the first and a second direction, the second direction being transverse to the first direction.

4. A pre-filter according to claim 1, wherein the first direction coincides with the flow direction.

5. A pre-filter according to claim 1, wherein the distance between the constrictions in the first direction varies in a random pattern.

6. A pre-filter according to claim 1, wherein the distance between the two opposed surfaces, at the constrictions, varies in a random pattern along the first direction.

7. A pre-filter according to claim 1, wherein a part of one of the surfaces comprises a closed-cell foam.

8. A pre-filter according claim 1, wherein substantially the entire surface of one of the surfaces comprises a closed-cell foam.

9. A pre-filter according to claim 7, wherein the outer surface of the closed-cell foam comprises a plurality of cavities.

10. A method of making a pre-filter according to claim 1, the method comprising the steps of:

providing an pre-filter element comprising an uneven surface, and assembling the pre-filter, such that the uneven surface defines one of the surfaces of the pre-filter.

11. A method according to claim 10, wherein the pre-filter element is a closed-cell foam.

12. An ostomy appliance comprising a collecting bag and a gas filtering assembly positioned in a gas path from an interior of the collecting bag to surroundings of the collecting bag, the gas filtering assembly comprising, in the flow direction of the gas from the interior to the surroundings, a pre-filter and a gas filter, wherein the pre-filter comprises a gas entrance, a gas exit, and a gas channel defined between the gas entrance and the gas exit, the gas channel having two opposed, at least substantially liquid impermeable surfaces defining there between a number of constrictions each having a predetermined, largest width, wherein the distance between the two opposed surfaces, at the constriction(s), is significantly smaller than the largest width of the constriction, wherein at least a part of the constrictions is provided in a random pattern.

* * * * *